(12) United States Patent
Makuuchi et al.

(10) Patent No.: US 9,261,475 B2
(45) Date of Patent: Feb. 16, 2016

(54) INSPECTION EQUIPMENT AND INSPECTION METHOD

(75) Inventors: Masami Makuuchi, Yokohama (JP); Minori Noguchi, Joso (JP); Hiroshi Kawaguchi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 430 days.

(21) Appl. No.: 13/701,678

(22) PCT Filed: Jun. 17, 2011

(86) PCT No.: PCT/JP2011/003458
§ 371 (c)(1),
(2), (4) Date: Jan. 29, 2013

(87) PCT Pub. No.: WO2012/029223
PCT Pub. Date: Mar. 8, 2012

(65) Prior Publication Data
US 2013/0187667 A1    Jul. 25, 2013

(30) Foreign Application Priority Data

Aug. 30, 2010    (JP) .................................. 2010-191632

(51) Int. Cl.
| | |
|---|---|
| *G01N 27/24* | (2006.01) |
| *H01M 10/42* | (2006.01) |
| *H01M 10/44* | (2006.01) |
| *H01M 10/48* | (2006.01) |
| *H01M 10/052* | (2010.01) |
| *H01M 10/058* | (2010.01) |

(52) U.S. Cl.
CPC ........... *G01N 27/24* (2013.01); *H01M 10/4285* (2013.01); *H01M 10/44* (2013.01); *H01M 10/48* (2013.01); *H01M 10/052* (2013.01); *H01M 10/058* (2013.01); *Y02T 10/7011* (2013.01)

(58) Field of Classification Search
None
See application file for complete search history.

(56) References Cited

U.S. PATENT DOCUMENTS

| | | | | |
|---|---|---|---|---|
| 3,805,156 | A | * | 4/1974 | Norton et al. ................. 324/683 |
| 4,707,887 | A | * | 11/1987 | Leifeld et al. .................... 19/0.2 |
| 6,346,819 | B1 | | 2/2002 | Joss et al. |
| 2002/0163342 | A1 | | 11/2002 | Ishioka et al. |
| 2003/0080755 | A1 | * | 5/2003 | Kobayashi ................... 324/658 |
| 2004/0046550 | A1 | * | 3/2004 | Kondo .......................... 324/233 |
| 2009/0303065 | A1 | * | 12/2009 | Lipowski ..................... 340/679 |

FOREIGN PATENT DOCUMENTS

| | | | |
|---|---|---|---|
| JP | 1-318948 | A | 12/1989 |
| JP | 8-16942 | B2 | 2/1992 |

(Continued)

OTHER PUBLICATIONS

International Search Report dated Sep. 27, 2011 (two (2) pages).

*Primary Examiner* — Melissa Koval
*Assistant Examiner* — Courtney McDonnough
(74) *Attorney, Agent, or Firm* — Crowell & Moring LLP

(57) ABSTRACT

Foreign metal inspection equipment is provided with: a conveying device for conveying a sample to be subjected to inspection; electrodes positioned so as to face the surface of the sample; a measurement device for measuring the capacitance between the electrodes and the sample being conveyed by the conveying device; and a processing unit that inspects for foreign metal mixed in the sample on the basis of the change in capacitance measured by the measurement device.

18 Claims, 7 Drawing Sheets

(56) References Cited

FOREIGN PATENT DOCUMENTS

| | | |
|---|---|---|
| JP | 6-34314 A | 2/1994 |
| JP | 10-239266 A | 9/1998 |
| JP | 11-316208 A | 11/1999 |
| JP | 2001-352147 A | 12/2001 |
| JP | 2002-5981 A | 1/2002 |
| JP | 2003-75412 A | 3/2003 |
| JP | 2003-185695 A | 7/2003 |
| JP | 2005-183142 A | 7/2005 |
| JP | 2008-46070 A | 2/2008 |
| JP | 2009-531604 A | 9/2009 |
| WO | WO 2007/109896 A1 | 10/2007 |

\* cited by examiner (DETECTION CIRCUIT (FOR ONE ELECTRODE))

(CHANGE IN CAPACITANCE)

(CHANGE IN CHARGING/DISCHARGING CURRENT)

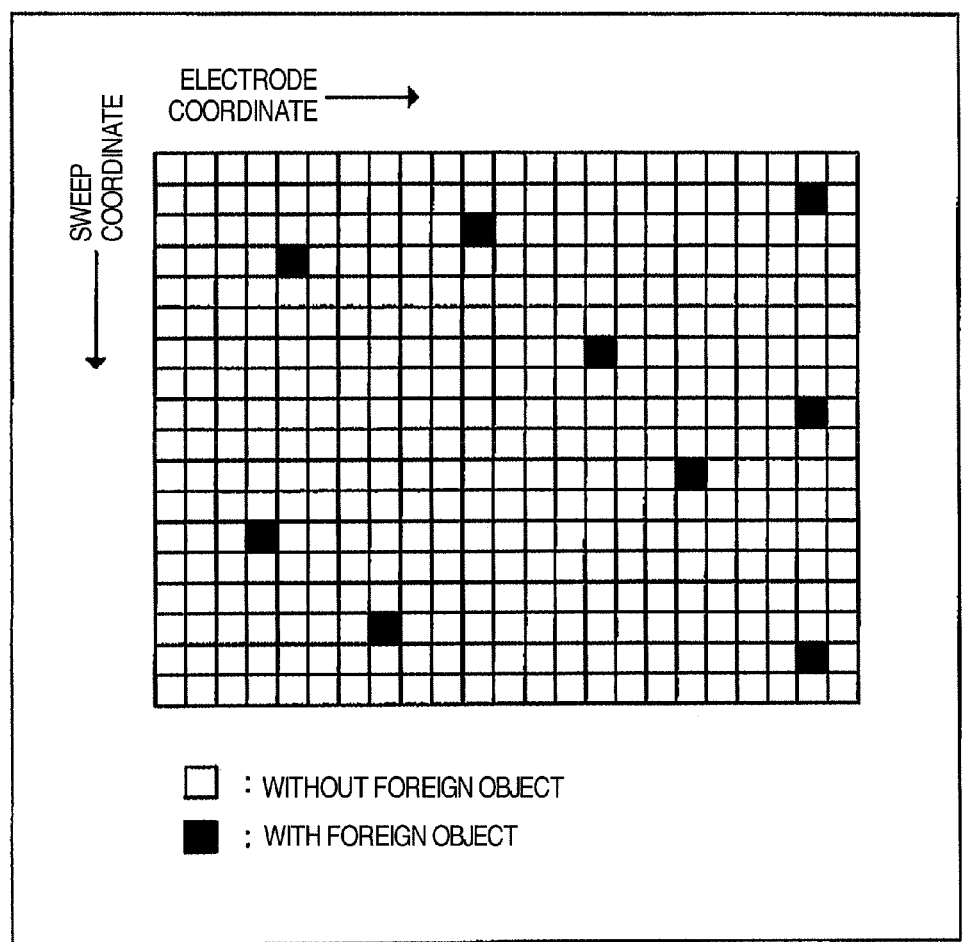

(DETECTION CIRCUIT (FOR ONE ELECTRODE))

(CHANGE IN CAPACITANCE)

(CHANGE IN CHARGING/DISCHARGING CURRENT)

(DETECTION CIRCUIT)

(OVERVIEW OF DETERMINATION OPERATION OF FOREIGN OBJECT)

INSPECTION EQUIPMENT AND INSPECTION METHOD

TECHNICAL FIELD

The present invention relates to an inspection of a defect of a sample and, in particular, relates to an inspection equipment and an inspection method for a metallic foreign object on metal.

BACKGROUND ART

It is known that, in the manufacturing process of a lithium battery, electrode materials are kneaded and, thereafter, a positive electrode medium such as lithium cobaltate is applied onto both sides of aluminum foil, which is a positive electrode, and dried and a negative electrode medium such as carbon material is applied onto both sides of copper foil, which is a negative electrode, and dried.

Here, when a battery is manufactured from the positive electrode and the negative electrode each having a respective medium applied thereto and dried (hereinafter, referred to as battery sheets), micro short-circuit occurs to deteriorate the battery performance significantly if a metallic foreign object is mixed in the battery sheet. Moreover, while the lithium battery is recently expected to be applied to electric vehicles, short-circuit might occur due to a metallic foreign object to cause catching fire or explosion and, thus, from a view point of preventing accidents caused by the lithium battery and of improving reliability, the importance of a metallic foreign object inspection with regard to a battery sheet is heightened.

As a prior art regarding a method for a foreign object inspection in an electrode material of a lithium battery, Patent Literature 1 (JP-A-2005-183142) discloses "a detection method for a foreign object causing magnetic turbulence in an electrode material for a lithium secondary battery, the method characterized in detecting existence of a foreign object causing magnetic turbulence in an electrode material for a lithium secondary battery formed in a thin film with use of a device that detects magnetic turbulence due to a magnetic impedance effect" (in CLAIMS).

Further, Patent Literature 2 (JP-A-2003-75412) discloses "a method for a defect detection for a film, the method characterized in, while applying a voltage in the thickness direction of the film with the rise time thereof being delayed, determining that the film contains a defect when a current flowing at this time exceeds a prescribed value."

CITATION LIST

Patent Literature

Patent Literature 1: JP-A-2005-183142
Patent Literature 2: JP-A-2003-75412

SUMMARY OF INVENTION

Technical Problem

With the method described in Patent Literature 1, when a moving speed of a magnetoresistive element is increased in order to detect a finer foreign object, it exceeds the response speed of a magnetic impedance sensor and, thus, the foreign object cannot be detected. Moreover, with the method described in Patent Literature 2, the only way to detect a finer foreign object is to increase the voltage and, thus, there are concerns on the destruction of an object to be inspected due to discharge and on the danger caused by high voltage.

Further, when there is a roughness in the surface of a manufactured metal or a non-uniformity in the thickness of an applied and dried medium or in the density of the medium, it results in a noise component in detecting a finer foreign object, thus making it difficult to detect the foreign object. In the methods described in Patent Literature 1 and Patent Literature 2, no specific methods are disclosed for detecting a foreign object in the state where this noise component is present, and there is a need to additionally provide a means to suppress the noise component so that a foreign object is detected.

Also, the manufacturing process needs to be monitored in order to manufacture a high quality metal. In order to monitor the manufacturing process, the position of a foreign object needs to be detected in addition to the existence of the foreign object; in the methods described in Patent Literature 1 and Patent Literature 2, a specific method regarding detection of the position of a foreign object is not disclosed and, thus, there is a need to additionally provide a measure capable of monitoring the manufacturing process.

An objective of the present invention is to provide an inspection equipment and an inspection method that contribute to achieving high reliability in metal manufacturing by providing a means to detect a fine metallic foreign object on metal with high accuracy. Also, by providing an inspection equipment and an inspection method that detect the existence of a metallic foreign object and the position thereof, it is to implement monitoring of mixing of a foreign object in the metal manufacturing process and to achieve reduction in costs due to reduction of manufacturing defects by early revision of the process.

Solution to Problem

The following explains briefly the outlines of typical inventions among the inventions disclosed in the present application.

(1) An inspection equipment for a metallic foreign object comprises: a moving device which moves a sample that is an object to be inspected; an electrode arranged at a position facing a surface of the sample; a measurement device which measures an electrostatic capacitance between the sample, which is in move by the moving device, and the electrode; and a processing part which inspects a metallic foreign object mixed in the sample based on a change in the electrostatic capacitance measured by the measurement device.

(2) An inspection method for a metallic foreign object comprises the steps of: moving a sample that is an object to be inspected; measuring an electrostatic capacitance between the sample and an electrode arranged at a position facing with respect to a surface of the sample, which is in move in the moving step; and processing to inspect a metallic foreign object mixed in the sample based on a change in the electrostatic capacitance measured in the measuring step.

Advantageous Effects of Invention

According to the present invention, an inspection equipment and an inspection method which implement detection of a metallic foreign object on metal with high accuracy can be provided.

BRIEF DESCRIPTION OF DRAWINGS

FIG. 3 is a monitor view showing a result of defect detection by the first embodiment of the foreign object inspection equipment according to the present invention;

DESCRIPTION OF EMBODIMENTS

Hereinafter, the embodiments of the present invention will be described in detail based on the accompanying drawings. In all the drawings for illustrating the embodiments, incidentally, the same reference sign is attached to the same element and repeated explanation thereof is omitted.

Embodiment 1

Figure 1:
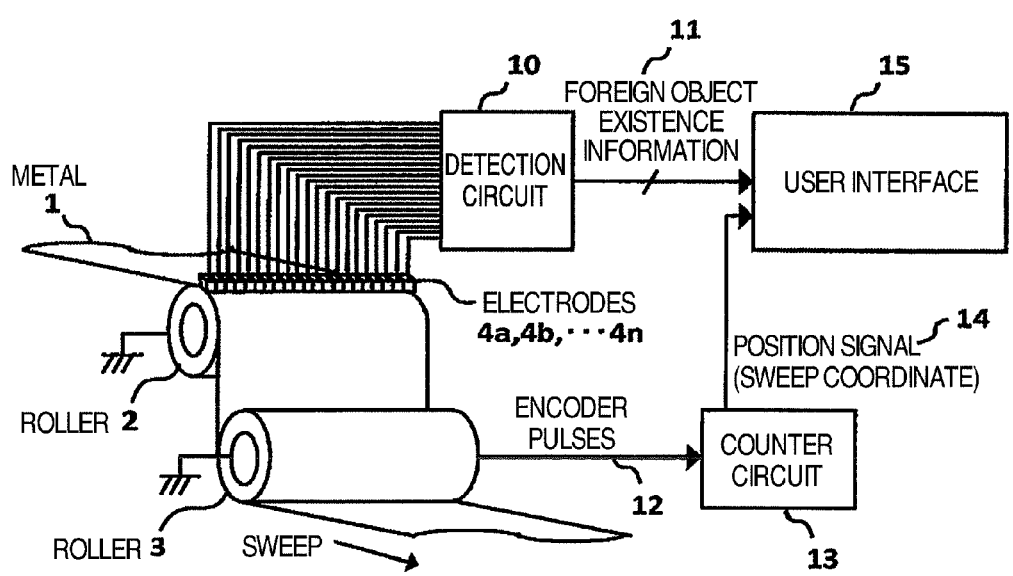
FIG. 1 is a configuration diagram of a first embodiment of a foreign object inspection equipment according to the present invention.

A first embodiment of a foreign object inspection equipment according to the present invention is described using FIGS. 1 to 3.

FIG. 1 is a configuration diagram of a first embodiment of the foreign object inspection equipment according to the present invention.

The foreign object inspection equipment of this embodiment is configured to comprise: rollers 2 and 3 for transferring a sample (metal 1) that is an object to be inspected; a plurality of electrodes 4a, 4b, ..., 4n arranged at positions facing a surface of the metal 1 transferred by the rollers 2 and 3; a detection circuit 10 that detects the existence of a foreign object by an electrostatic capacitance between each of the plurality of electrodes 4a, 4b, ..., 4n and the metal 1; a counter circuit 13 that counts the number of pulses based on encoder pulses 12 generated by rotation action of the roller 3; and a user interface 15 that outputs whether or not a foreign object is present on the metal 1 and at which position a foreign object is using foreign object existence information 11 output by the detection circuit 10 and a position signal (sweep coordinate) 14 output by the counter circuit 13.

Here, the metal 1 is an object to be inspected and the present invention relates to a foreign object inspection equipment which detects defects and/or foreign objects present in the metal 1. Here, the defects include scratches, cracks, and the like.

The rollers 2 and 3 rotate so as to sweep the metal 1.

Figure 7:
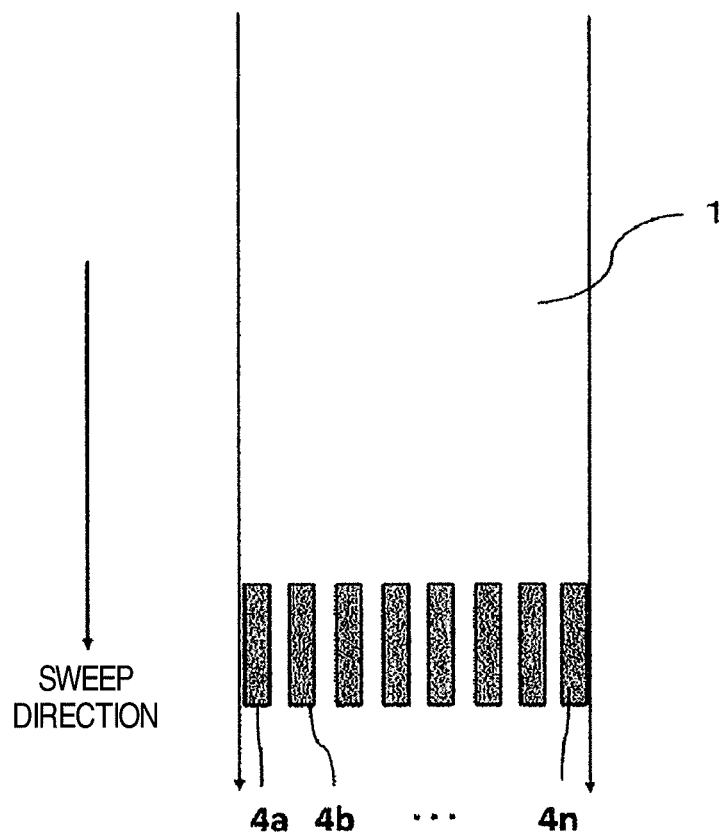
FIG. 7 is a diagram illustrating an arrangement of electrodes of the first embodiment of the foreign object inspection equipment according to the present invention.

FIG. 7 is a diagram illustrating an arrangement of electrodes of the first embodiment of the foreign object inspection equipment according to the present invention. The arrangement of the electrodes is described using FIG. 7. The plurality of the electrodes 4a, 4b, ..., 4n are arranged so as to face a surface of the metal 1 and are arranged side by side in a direction normal to a direction of sweep by the roller 2.

The detection circuit 10 detects respective electrostatic capacitance values of the plurality of the electrodes 4a, 4b, ..., 4n. The electrostatic capacitance is described later; it is a capacitance C obtained in accordance with the distance between the metal 1 and each of the electrodes 4a, 4b, ..., 4n. Further, after detecting the electrostatic capacitance value, it processes the detection value and sends to the user interface 15 the foreign object existence information 11 indicating whether or not a defect or a foreign object is present in the metal 1.

The counter circuit 13 counts the number of pulses based on the encoder pulses 12 generated by the rotation action of the roller 3. Thus, it determines a position in the surface of the metal 1, at which the electrostatic capacitance is being detected with the plurality of the electrodes 4a, 4b, ..., 4n, and sends the sweep coordinate facing the plurality of the electrodes 4a, 4b, ..., 4n to the user interface 15 as a position signal.

The user interface 15 displays whether or not a defect or a foreign object is present in the metal 1 and also its position if present based on the foreign object existence information 11 transmitted from the detection circuit 10 and the position signal (sweep coordinate) 14 transmitted from the counter circuit 13. Incidentally, the output device of the user interface 15 may be a display used with an ordinary computer or a touch panel or may be via a communication means; regardless of the type of the device, it is not illustrated. Moreover, in the configuration of the foreign object inspection equipment shown in FIG. 1, it is clear that a user may set conditions for foreign object determination in the detection circuit 10 via the user interface 15 and it is not illustrated here; furthermore, an input function in the user interface 15 may be a keyboard used with an ordinary computer or a touch panel or may be an input function via a communication means and regardless of the type of the device it is not illustrated.

Figure 2A:
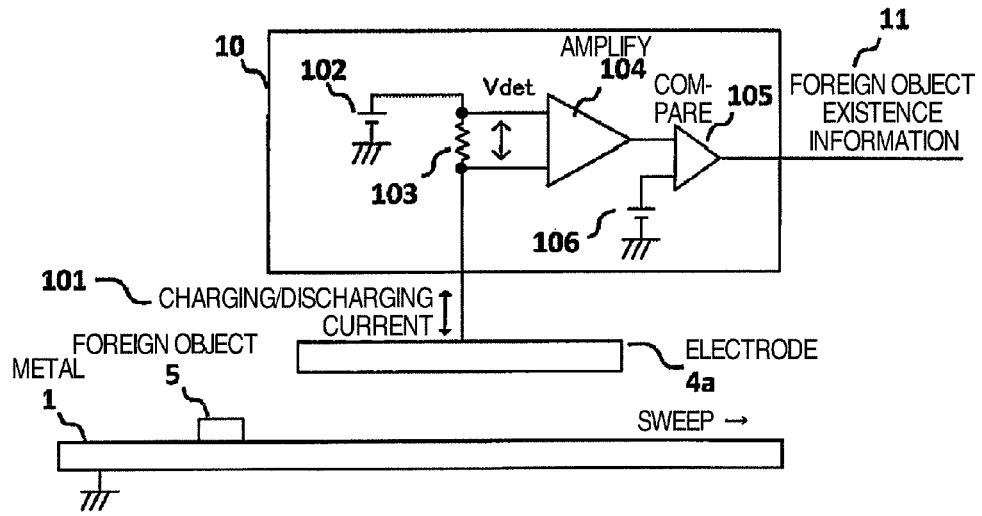
FIG. 2A is a diagram illustrating a detection principle of the first embodiment of the foreign object inspection equipment according to the present invention.
Figure 2B:
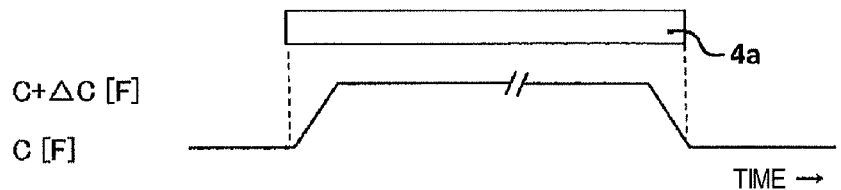
FIG. 2B is a diagram illustrating the detection principle of the first embodiment of the foreign object inspection equipment according to the present invention.
Figure 2C:
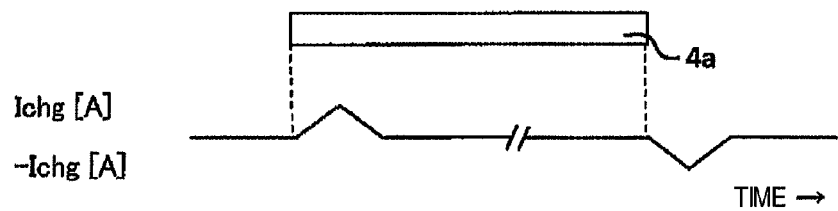
FIG. 2C is a diagram illustrating the detection principle of the first embodiment of the foreign object inspection equipment according to the present invention.

FIGS. 2A to 2C are diagrams illustrating a detection principle of the first embodiment of the foreign object inspection equipment according to the present invention.

For simplicity of description, out of the foreign object inspection equipment, in which the plurality of the electrodes 4a, 4b, ..., 4n shown in FIG. 1 are arranged, a schematic configuration of the detection circuit 10 for one electrode (4a) is shown in FIGS. 2A to 2C. The side views of a metal 1, a foreign object 5 present on the metal 1, the electrode 4a arranged so as to face a surface of the metal 1, and the detection circuit 10 are shown.

The electrode 4a arranged facing the transferred metal 1 is connected to a voltage source 102 via a resistor 103 equipped in the detection circuit 10. While the metallic foreign object 5 is present on the metal 1 and is passing under the electrode 4a, the gap between the metal 1 connected to the earth potential and the electrode 4a changes and a capacitance C configured with the metal 1 and the electrode 4a changes to C+ΔC as shown in FIG. 2B. As the capacitance C changes, a charging/discharging current 101 to/from the electrode 4a flows as shown in FIG. 2C and a voltage Vdet is induced between the both ends of the resistor 103.

In the detection circuit 10, an amplifier circuit 104 is connected to the both ends of the resistor 103 and amplifies the voltage Vdet induced by the change in the capacitance; in a comparator circuit 105, the output voltage of the amplifier circuit 104 and a comparison voltage 106 are compared with each other and, when the output voltage of the amplifier circuit 104 is higher than the comparison voltage 106, for example, it is regarded that a foreign object is present and a signal indicative of presence of a foreign object is output as the foreign object existence information 11.

In FIG. 2A, for simplify of the explanation of the detection principle, a configuration has been described in which the induced voltage Vdet of the resistor 103 is amplified by the amplifier circuit 104; it is needless to say, however, that it may be configured by a current-voltage conversion circuit. Moreover, although in FIG. 2A an example is illustrated in which one comparison voltage 106 and the output voltage of the amplifier circuit 104 are compared with each other in the comparator circuit 105, the comparison with a plurality of voltages may be employed or the comparison operation may be performed with sampling data using an analog-to-digital-conversion circuit.

FIG. 3 is a monitor view showing a result of defect detection by the first embodiment of the foreign object inspection equipment according to the present invention.

The electrode coordinate of the abscissa corresponds to the electrode coordinate that is the position of each of the electrodes 4a, 4b, ..., 4n and the sweep coordinate corresponds to the electrode position on the swept metal 1 based on the position signal (sweep coordinate) 14 from the counter circuit 13.

In the screen, a black portion is a portion in which it is determined by the detection circuit 10 that a foreign object is present, and a white portion is a portion in which it is determined that a foreign object is not present. In this manner, by the user interface 15, the existence of a foreign object and a coordinate position of a foreign object in the metal 1 can be known.

Embodiment 2

Figure 4A:
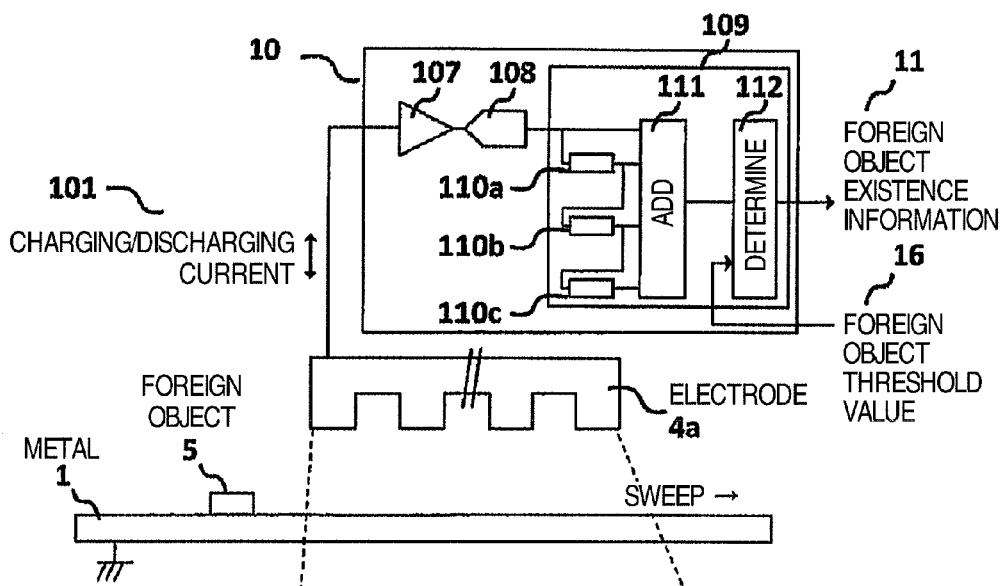
FIG. 4 is a diagram illustrating a detection principle of a second embodiment of the foreign object inspection equipment according to the present invention.
Figure 4B:
Figure 4C:

A second embodiment of the foreign object inspection equipment according to the present invention is described using FIGS. 4A to 4C.

FIGS. 4A to 4C are diagrams illustrating a detection principle of the second embodiment of the foreign object inspection equipment according to the present invention.

In the following, differences from the detection principle of the first embodiment described with FIGS. 2A to 2C are mainly explained. In the foreign object inspection equipment shown in FIG. 4A, the electrode 4a, the surface of which facing the metal 1 is formed in an uneven shape of a periodic interval, is arranged, and the output from the electrode 4a is connected to a current-voltage conversion circuit 107. As a foreign object 1 passes under the electrode 4a, the capacitance formed with the electrode 4a and the metal 1 periodically changes between C and C+ΔC as shown in FIG. 4B and the charging/discharging current 101 flowing between the electrode 4a and the current-voltage conversion circuits 107 results in a periodic signal shown in FIG. 4C.

In the detection circuit 10, an output signal of the current-voltage conversion circuit 107 is sampled by an analog-to-digital-conversion circuit 108 and addition operations are performed in an addition circuit 111 via delay circuits 110a, 110b, and 110c arranged in a signal processing circuit 109. In the case of a fine foreign object, the charging/discharging current is very small and, thus, detection becomes difficult due to influences of noises.

It is generally known that addition processing of signals is effective in order to suppress influences of noises; based on the periodic signal generated from one foreign object, influences of noises in signal detection can be suppressed by delaying the signal sequentially with the delay circuits 110a, 110b, and 110c and performing addition processing. Subsequently, in a decision circuit 112, the output of the addition circuit 111 is compared with a foreign object threshold value 16 from the user interface 15 (not shown) and the foreign object existence information 11 is output to the user interface 15.

Embodiment 3

Figure 5:
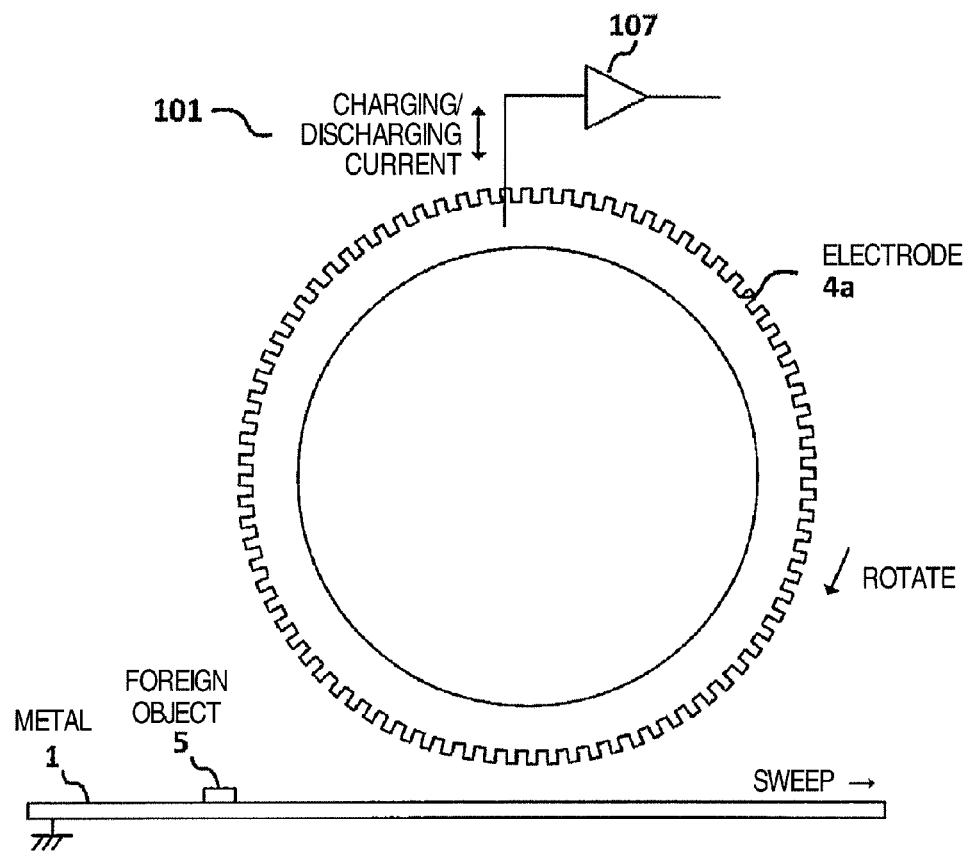
FIG. 5 is a diagram showing a configuration of electrodes of a third embodiment of the foreign object inspection equipment according to the present invention.

A third embodiment of the foreign object inspection equipment according to the present invention is described using FIG. 5.

FIG. 5 is a diagram showing a configuration of electrodes of the third embodiment of the foreign object inspection equipment according to the present invention.

In the following, differences from the detection principle of the second embodiment described in FIG. 4 are mainly explained. The electrode 4a shown in FIG. 5 is made so that its side facing the metal 1 is formed in an uneven shape of a periodic interval and it is further formed in a ring shape, and the charging/discharging current 101 to/from the electrode 4a is converted into a voltage by the voltage-current conversion circuit 107. Here, by letting a time for the foreign object 5 present on the metal 1 to pass under one of convex portions of the electrode 4a be Δt, a change in the capacitance configured with the metal 1 and the electrode 4a be ΔC, and a potential difference between the metal 1 and the electrode 4a be V, the charging/discharging current Δi flowing in the electrode 4a is expressed by the following Math. 1.

[MATH. 1]

$$\Delta i = \Delta C \Delta V / \Delta t. \tag{1}$$

Accordingly, when a foreign object is minute as it passes under the electrode 4a, the change amount of the capacitance ΔC becomes small and, if the potential V and a time to pass Δt are constant, consequently, the charging/discharging current Δi becomes small so that detection of a foreign object becomes difficult. In the present embodiment, by rotating the electrode 4a formed in a ring shape in the direction opposite to the sweep direction of the metal 1 with a rotating mechanism (not shown) and reducing the time Δt for a foreign object to pass under one of convex portions of the electrode 4a, the charging/discharging current Δi can be increased even when the foreign object is minute so that detection of a fine foreign object can be implemented.

Embodiment 4

Figure 6A:
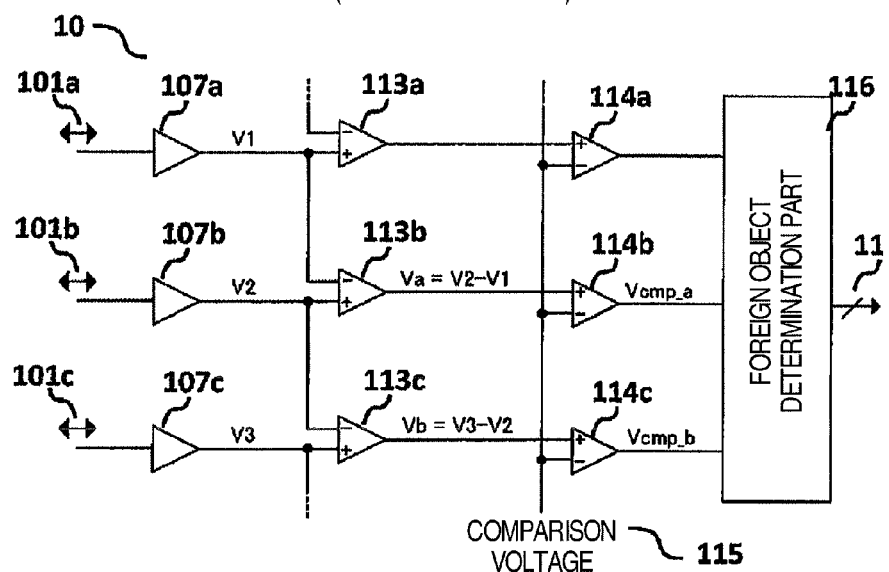
FIG. 6A is a diagram illustrating a detection principle of a fourth embodiment of the foreign object inspection equipment according to the present invention.
Figure 6B:
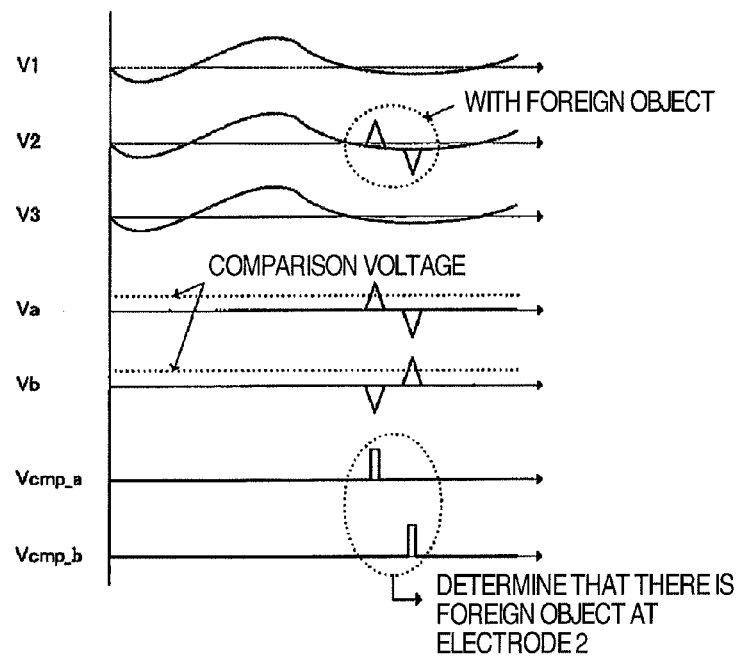
FIG. 6B is a diagram illustrating the detection principle of the fourth embodiment of the foreign object inspection equipment according to the present invention.

Using FIGS. 6A and 6B, a fourth embodiment of the foreign object inspection equipment according to the present invention is described.

FIGS. 6A and 6B are diagrams illustrating a detection principle of the fourth embodiment of the foreign object inspection equipment according to the present invention.

In the detection circuit 10 shown in FIG. 6A, current-voltage conversion circuits 107a, 107b, and 107c connected to a plurality of electrodes (not shown) are arranged and charging/discharging currents 101a, 101b, and 101c are converted into voltages, respectively. Subsequently, in subtraction circuits 113a, 113b, and 113c, the output voltages of the current-voltage conversion circuits 107a, 107b, and 107c are subject to subtraction processing.

For example, in the subtraction circuit 113b, a voltage Va is obtained from an output voltage V1 of the current-voltage conversion circuit 107a and an output voltage V2 of the current-voltage conversion circuit 107b through subtraction processing. In comparator circuits 114a, 114b, and 114c, the respective output voltages of the subtraction circuits 113a, 113b, and 113c are compared with a comparison voltage 115, the existence of a foreign object is determined in a foreign object determination part 116 based on the outputs of the comparator circuits 114a, 114b, and 114c, and the foreign object existence information 11 is output to the user interface 15 (not shown).

When there is a roughness in the surface of the metal 1 or when there is a non-uniformity in the thickness or a non-uniformity in the density of the medium applied to the metal 1 and dried, the output voltages of the current-voltage conversion circuits 107a, 107b, and 107c become signals as indicated by V1, V2, and V3 of FIG. 6B and it thus becomes difficult to detect a fine foreign object. By taking differences of the detection signals V1, V2, and V3 between adjacent electrodes in the subtraction circuits 113a, 113b, and 113c, signals Va and Vb with signal components other than that of a foreign object suppressed are generated, so that existence of a foreign object can be detected in the foreign matter determination part 116 from Vcmp_a and Vcmp_b, which are the results of comparison with the comparison voltage 115 in the comparator circuits 114a, 114b, and 114c.

With the foreign object inspection equipment and the inspection method according to the present invention, detection of a fine metallic foreign object on a metal with high accuracy can be implemented and reliability of metal manufacturing can be improved. Also, monitoring of mixture of a foreign object in metal manufacturing process can be realized and cost reduction due to reduction of manufacturing defects by an early revision of the process can be implemented.

REFERENCE SIGNS LIST 1 metal to be inspected
2, 3 rollers
4a, 4b, . . . , 4n electrodes
5 foreign object
10 detection circuit
11 foreign object existence information
12 encoder pulses
13 counter circuit
14 position signal
15 user interface
16 foreign object threshold value
101, 101a, 101b, 101c charging/discharging currents
102 voltage source
103 resistor
104 amplifier circuit
105 comparator circuit
106 comparison voltage
107, 107a, 107b, 107c current-voltage conversion circuits
108 analog-to-digital-conversion circuit
109 signal processing circuit
110a, 110b, 110c delay circuits
111 addition circuit
112 decision circuit
113a, 113b, 113c subtraction circuits
114a, 114b, 114c comparator circuits
115 comparison voltage
116 foreign object determination part

The invention claimed is:

1. An inspection equipment for a metallic foreign object comprising:
   a moving device which moves a sample that is an object to be inspected;
   an electrode arranged at a position facing a surface of the sample;
   a measurement device which measures an electrostatic capacitance between the sample, which is moved by the moving device, and the electrode; and
   a processing part which inspects a metallic foreign object mixed in the sample based on a change in the electrostatic capacitance measured by the measurement device,
   wherein the electrode is one of plural electrodes forming a ring, the ring is rotated while facing the surface of the sample with a space therebetween, and a rotating direction of the ring is opposite to a sweep direction of the sample.

2. The inspection equipment according to claim 1, wherein in the processing unit the metallic foreign object is inspected by adding a plurality of electrostatic capacitances measured from each of the plural electrodes.

3. The inspection equipment according to claim 1, wherein in the processing unit existence of a metallic foreign object and a position thereof are inspected.

4. The inspection equipment according to claim 1, wherein the moving device translates so that the one electrode corresponds to a thin film on the surface of the sample.

5. The inspection equipment according to claim 1, wherein the sample moved by the moving device is not in contact with the one electrode.

6. The inspection equipment according to claim 1, further comprising a display device which displays a position of a foreign object.

7. The inspection equipment according to claim 1, wherein in the measurement device a charging/discharging current corresponding to a change in the electrostatic capacitance between the sample and the one electrode is detected.

8. The inspection equipment according to claim 1, wherein the one electrode comprises a periodic unevenness on a surface facing the sample.

9. The inspection equipment according to claim 2, wherein the plural electrodes are arranged in a form of a toothed wheel and rotate so as to constantly face a thin film.

10. An inspection method for a metallic foreign object, the method comprising the steps of:
    moving a sample which is an object to be inspected;
    measuring an electrostatic capacitance between the sample and an electrode arranged at a position facing with respect to a surface of the sample, which is moved in the moving step; and
    processing to inspect a metallic foreign object mixed in the sample based on a change in the electrostatic capacitance measured in the measuring step,
    wherein the electrode is one of plural electrodes forming a ring, the ring is rotated while facing the surface of the sample with a space therebetween, and a rotating direction of the ring is opposite to a sweep direction of the sample.

11. The inspection method according to claim 10, wherein in the processing step the metallic foreign object is inspected by adding a plurality of electrostatic capacitances measured from each of the plural electrodes.

12. The inspection method according to claim 10, wherein in the processing step existence of a metallic foreign object and a position thereof are inspected.

13. The inspection method according to claim 10, wherein in the moving step the one electrode translates so as to correspond to a thin film on the surface of the sample.

14. The inspection method according to claim 10, wherein the sample moved in the moving step is not in contact with the one electrode.

15. The inspection method according to claim 10, further comprising the step of displaying a position of a foreign object.

16. The inspection method according to claim 10, wherein in the measuring step a charging/discharging current corresponding to a change in the electrostatic capacitance between the sample and the one electrode is detected.

17. The inspection method according to claim 10, wherein the one electrode comprises a periodic unevenness on a surface facing the sample.

18. The inspection method according to claim 11, wherein the plural electrodes are arranged in a form of a toothed wheel and rotate so as to constantly face a thin film.

\* \* \* \* \*